(12) United States Patent
Benner et al.

(10) Patent No.: US 10,055,870 B2
(45) Date of Patent: Aug. 21, 2018

(54) METHOD AND SYSTEM FOR DISPLAYING AN AUGMENTED REALITY TO AN OPERATOR OF A MEDICAL IMAGING APPARATUS

(71) Applicant: Siemens Healthcare GmbH, Erlangen (DE)

(72) Inventors: Thomas Benner, Erlangen (DE); Andreas Potthast, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 91 days.

(21) Appl. No.: 15/255,191

(22) Filed: Sep. 2, 2016

(65) Prior Publication Data

US 2017/0069120 A1 Mar. 9, 2017

(30) Foreign Application Priority Data

Sep. 3, 2015 (DE) .......................... 10 2015 216 917

(51) Int. Cl.

| | |
|---|---|
| *G09G 5/00* | (2006.01) |
| *G06T 11/60* | (2006.01) |
| *A61B 8/00* | (2006.01) |
| *G06F 3/01* | (2006.01) |
| *A61B 90/00* | (2016.01) |
| *A61B 5/00* | (2006.01) |
| *A61B 5/055* | (2006.01) |

(52) U.S. Cl.
CPC .............. *G06T 11/60* (2013.01); *A61B 5/743* (2013.01); *A61B 5/7425* (2013.01); *A61B 8/00* (2013.01); *G06F 3/013* (2013.01); *A61B 5/0035* (2013.01); *A61B 5/0059* (2013.01); *A61B 5/055* (2013.01); *A61B 5/704* (2013.01); *A61B 2090/365* (2016.02); *A61B 2562/0219* (2013.01)

(58) Field of Classification Search
None
See application file for complete search history.

(56) References Cited

U.S. PATENT DOCUMENTS

| | | | |
|---|---|---|---|
| 2002/0082498 A1 | 6/2002 | Wendt et al. | |
| 2005/0206583 A1 | 9/2005 | Lemelson et al. | |
| 2009/0021257 A1* | 1/2009 | Yasuhara | G01R 33/283 324/318 |
| 2017/0323062 A1* | 11/2017 | Djajadiningrat | G06F 19/34 |

\* cited by examiner

*Primary Examiner* — Frank Chen
(74) *Attorney, Agent, or Firm* — Schiff Hardin LLP

(57) ABSTRACT

In a method for automatically supporting an operator in working through an execution sequence protocol with a number of sequence steps, with which a person under examination is being examined in a medical imaging facility, the execution sequence protocol to be carried out for the person under examination is determined, and image data are acquired that show a field of vision of at least a part of the environment of the medical imaging facility and the person under examination, as seen by the operator. A next sequence step of the execution sequence protocol is determined that is to be carried out by the operator. Visual information is created that will inform the operator about the operating step to be carried out, and the visual information is project at a viewing facility for displaying an augmented reality to the operator, in which the field of vision is presented augmented by the visual information.

22 Claims, 5 Drawing Sheets

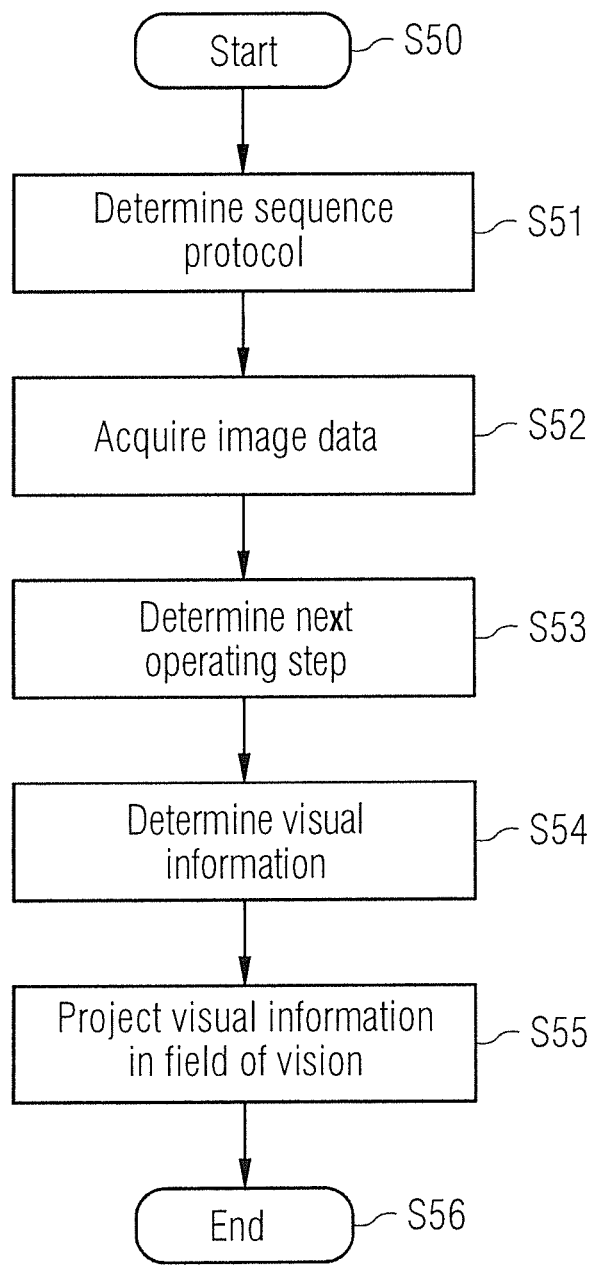

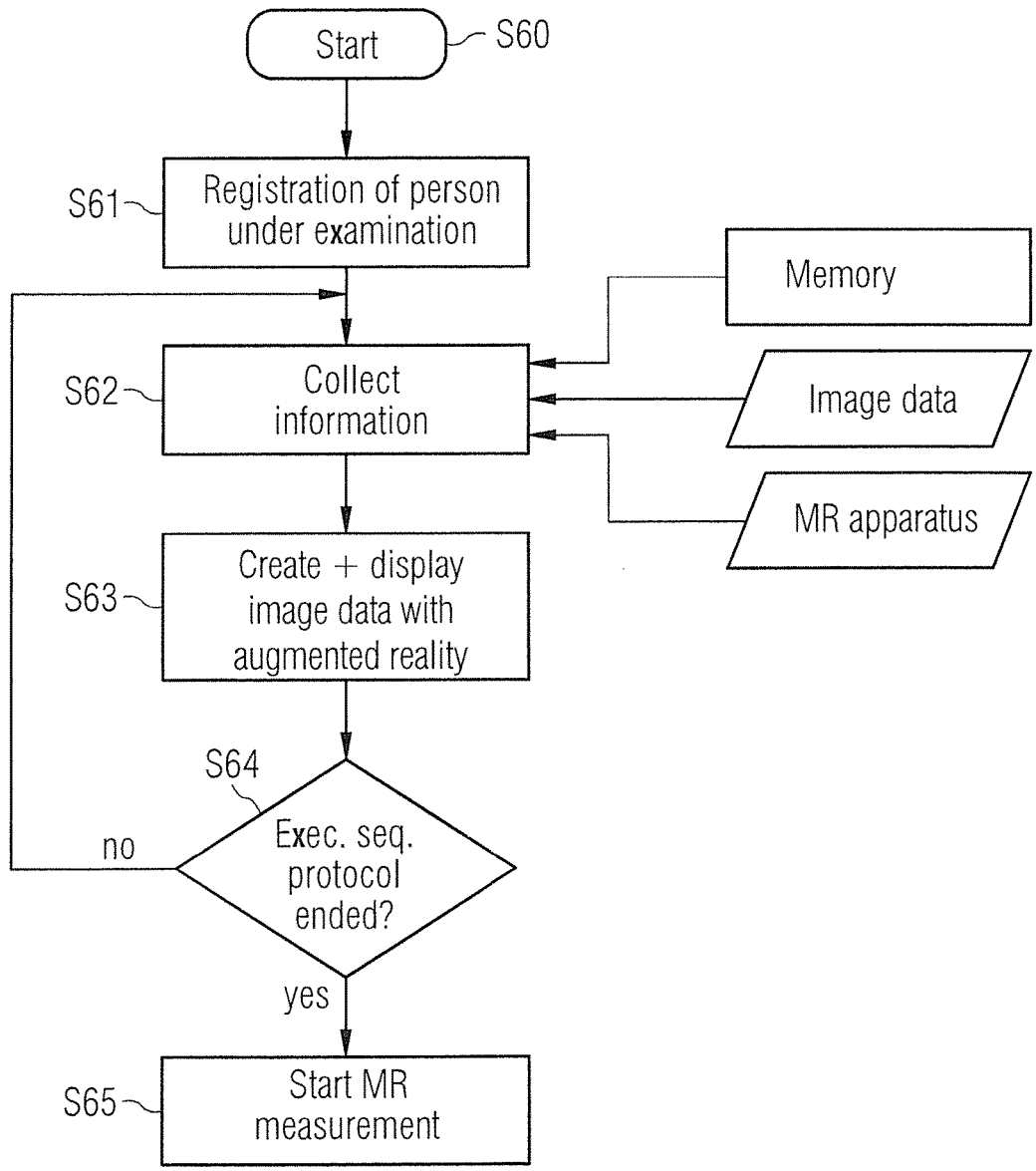

METHOD AND SYSTEM FOR DISPLAYING AN AUGMENTED REALITY TO AN OPERATOR OF A MEDICAL IMAGING APPARATUS

BACKGROUND OF THE INVENTION

Field of the Invention

The present invention concerns a method and a system for assisting an operator in the operation of a medical imaging apparatus.

Description of the Prior Art

Medical imaging facilities, such as Computed Tomography (CT) systems and Magnetic Resonance (MR) apparatuses offer the user a very broad spectrum of opportunities for creating images of an object under examination, such as a patient. The operation of such an imaging facility is heavily dependent on whether there are experienced personnel on site who are capable of operating such facilities without errors. In the operation of MR apparatuses, for example, different aspects must be taken into account, such as the positioning of the RF coils, the support of the person under examination, the attachment and connection of additional devices for physiological monitoring of the patient (ECG, respiration belt), the choice of the imaging sequences, etc.

Furthermore therapeutic measures or interventional applications are carried out in conjunction with medical imaging facilities, for removal of tissue or for performing small operations for example. The person carrying out such procedures can need yet further instruments or devices for this purpose. All these instruments or devices must be at hand in the right place, so that a smooth sequence of the examination can be insured.

Trained operators are important for the smooth execution of such examinations, and this training must be carried out on an ongoing basis.

Manuals or handbooks in paper or electronic format are known, which can help the operator in the operation of the imaging facility. In practice, however, such operating instructions are impractical during preparation for imaging, since they need to be physically carried by the operator. For the wellbeing of the person under examination and for economic reasons, it is desirable to minimize the time that the person under examination spends in the imaging facility, as well to minimize errors during operation.

SUMMARY OF THE INVENTION

An object of the present invention is to improve the operation of a medical imaging facility. In particular the object is to enable the operator to rapidly recognize which further operating step is to be executed in an execution sequence protocol that has multiple execution steps, so that errors occur less often during operation.

In accordance with a first aspect of the invention, this object is achieved by a method for automatically assisting an operator in working through an execution sequence protocol with a number of sequence steps, wherein a person is examined in a medical imaging facility with the execution sequence protocol. The method begins by the execution sequence protocol to be carried out being defined for the person under examination. Furthermore, image data are acquired that shows a field of vision, as seen by the operator, that encompasses at least a part of the environment of the medical imaging facility and the person under examination. A next execution step of the execution sequence protocol is determined, in which an operating step is to be carried out by the operator. Visual information is created with which the operator is informed about the operating step to be carried out. This visual information is projected in a visual presentation facility that displays an augmented reality into the field of vision of the operator, with the field of vision being shown augmented by the visual information.

Through the use of a system with a visual facility for displaying such an augmented reality, the operator can be informed intuitively and in a simple manner about the next step. The next operating step to be carried out is projected as visual information into the field of vision. The operator can then carry out the next operating step without errors, by following the visual information. The image data that show the field of vision as seen by the operator can contain the medical imaging facility, for example, with a position and orientation of the medical imaging facility being determined in the image data. Furthermore a viewing position of the operator is detected from which the operator sees the field of vision, wherein the viewing position is determined while taking account of the determined position and orientation of the medical imaging facility. In order to project the visual information for the operator correctly into the field of vision it is of advantage to know the precise viewing position, i.e. the position from which the operator is observing what is happening. For this purpose, objects or markings in the acquired image data must be recognized, in order to deduce the viewing position and the field of vision from the location of the recognized objects. The medical imaging facility itself is a prominent object, and the viewing position can be deduced by the position and orientation of the imaging facility. The form (outline) of the imaging facility is largely defined, so that the viewing position and the field of vision can be deduced from the location of the imaging facility.

Furthermore a positioning of the person under examination relative to the medical imaging facility can be determined automatically from the execution sequence protocol, with the positioning of the person under examination relative to the medical imaging facility being projected as visual information into the viewing facility. Which part of the person under examination is to be examined can usually be taken from an execution sequence protocol for the imaging facility. For example, if images of the knee or of the head are to be recorded, this is recognizable from the execution sequence protocol. When the region to be examined is known, it can also be deduced how the person under examination must be positioned relative to the imaging facility. This can be projected as visual information into the field of vision for example, so that the operator can perform the supporting of examination position correctly.

As well as the visual information, it is also possible to define personal information that provides information about the person under examination, wherein this personal information is likewise projected into the field of vision. The name of the person under examination can be projected as personal information into the field of vision, for example. This information can help the operator improve the overall execution sequence, since this information can be useful for a few of the operating steps.

It is likewise possible for the additional devices that are needed for carrying out the execution sequence protocol to be determined automatically from the determined execution sequence protocol. For this purpose, device information about the additional devices needed can be created and projected into the viewing facility. For example it can be necessary for the examination to monitor certain physiological parameters such as the heartbeat or the breathing, or it is necessary to inject contrast medium. The devices needed for this can be determined from the execution sequence protocol. Through the device information, the operator knows immediately which additional devices are necessary for the execution sequence of the examination. It can be determined here for example, on the basis of the acquired image data or from information of the imaging facility, which of the additional devices are already arranged ready for operation in the field of vision or operator. Then the devices still missing can be determined, wherein the projected device information then only provides information about the devices that are still missing or are not yet in the right position.

On the basis of the acquired image data of the environment of the imaging facility, it is also possible to check the data as to whether an operating error is represented in the image data. Such an operator error is a situation for the medical imaging facility or the person under examination that does not match the execution sequence protocol. If such a situation is discovered in the image data, error information can be determined and projected into the field of vision. For example, if it has been recognized that the person under examination is not correctly located, for example feet first instead of head first, then this can be highlighted by the viewing facility in the field of vision and identified as incorrect, or the correct location can be projected by the viewing facility into the field of vision.

Likewise, the next operating step to be carried out can be converted into audio information and played to the operator.

Furthermore a current status of the medical imaging facility can be determined, wherein status information that is projected into the field of vision as well as the visual information, which is projected into the field of vision along with the visual information, is determined from this current status. For example it can be recognized on the basis of the image data which operating steps or execution sequence steps of the protocol have already been carried out and which steps are still missing. The steps already carried out or the steps still missing can be projected accordingly into the field of vision of the operator.

When the medical imaging facility is an MR apparatus, it is possible that the positioning of an RF coil on the person under examination is necessary as the next operating step to be carried out. The visual information projected into the field of vision projected can then contain a positioning of the RF coil relative to the MR apparatus and the person under examination. The positioning of the coil on the person under examination and relative to the MR apparatus forms a frequent source of errors. These errors can be improved by the visual presentation of how the coil is to be fastened to the person under examination and the MR apparatus.

The invention likewise concerns a system for displaying augmented reality as described above, which has a viewing facility for the operator, into which the visual information is projected. Furthermore an image acquisition unit is provided for acquiring the image data and a processor unit that is embodied for executing the steps carried out above.

BRIEF DESCRIPTION OF THE DRAWINGS

FIG. 5 is a flowchart of the steps that can be carried out in the system for displaying the augmented reality in accordance with the invention.

FIG. 6 is a flowchart with the steps for operating an MR apparatus from FIG. 1, using the system for displaying the augmented reality in accordance with the invention.

DESCRIPTION OF THE PREFERRED EMBODIMENTS

It is explained below how, with the use of a system for displaying the augmented reality, the operation of a medical imaging facility can be simplified, so that in particular fewer operating errors occur and the period of time for the operation is minimized.

The following description of the forms of embodiment is given in conjunction with an MR apparatus as medical imaging facility. Naturally, however, the present invention can also be used for other medical imaging facilities, such as for CT for example of any other medical imaging facility such as an x-ray apparatus.

Figure 1:
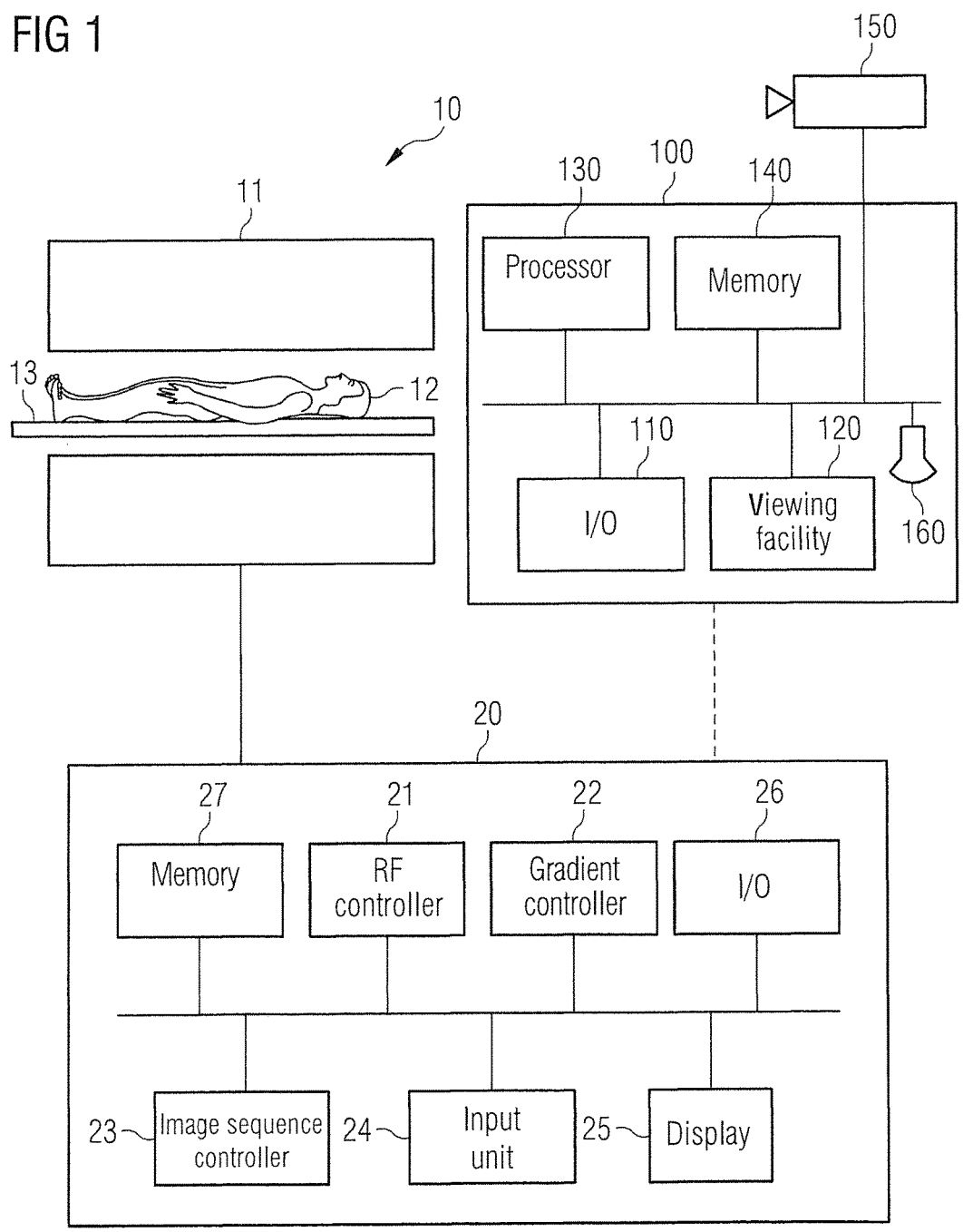
FIG. 1 schematically shows an arrangement in which a system for displaying the augmented reality in accordance with the invention is used in an MR apparatus.

FIG. 1 shows schematically an MR apparatus 10 with a scanner 11 that includes a basic field magnet for creating a polarization field B0. A person under examination 12, lying on a table 13, can be moved into the scanner 11. The MR apparatus 10 has a control computer 20 with an RF controller 21 for controlling the radiation of RF pulses, as well as a gradient controller 22 for controlling the switching of the magnetic field gradients during the imaging. An image sequence controller 23 is responsible for the control of the chronological sequence of the use of the RF pulses and magnetic field gradients as a function of the selected imaging sequence, so that the image sequence controller 23 also checks and controls the RF controller 21 and the gradient controller 22. Furthermore, an input unit 24 is provided, with which an operator can control the MR apparatus. The input unit 24 has a keyboard, a touch-sensitive screen, a mouse or the like. On a display monitor 25, the examinations can be planned and the created MR images displayed. Via an input/output interface 26, the MR apparatus 10 can communicate with further units, for example with a system 100 for displaying an augmented reality, which will be described in detail below. Various execution sequence protocols that are needed for recording MR images of different anatomical regions can be stored in a memory 27.

The manner by which MR images are created in the MR apparatus by switching of RF pulses, magnetic field gradients and detection of the MR signals is known to those skilled in the art and thus need not be explained in detail herein. The system 100 for displaying the augmented reality has an input and output interface 110, with which the system can communicate inter alia with other facilities, such as for example the MR apparatus 10. The communication link between the system 100 and the MR apparatus 10 can be wired or wireless. The connection between the central control computer 20 and the components in the vicinity of the magnet is preferably a cable connection. The system 100 also has a viewing facility 120. For example the viewing facility can be a pair of eyeglasses or a similar facility that the operator wears, and into which visual information can be projected, as will be explained in detail below. The system further has a processor 130 (that can be one or more processors). The processor 130 is responsible for the way in which the system functions and controls the execution sequence of the individual functional components between one another as well as the way in which the system as a whole functions. Program codes can be stored in a memory 140 for example wherein, when the program code is executed by the processor 130, the steps of the system 100 that have been explained above and that will be explained in greater detail further below can be executed. An image acquisition detector 150 is provided, which acquires image data that shows a field of view of the operator. The image acquisition detector 150, for example a CCD camera or the like, can be attached to the operator's head for example, so as to acquire image data that is similar to the field of vision of the operator, so that the field of vision of the operator can be deduced. Furthermore the system can have at least one speaker 160 for emitting an audio signal, so the operator is informed not only visually, but also via audio information, about the next operating step to be carried out. The system 100 is preferably a wearable system, in particular the viewing facility 120 and the image acquisition detector 150 are embodied as a wearable system and can be worn by the operator as a helmet or eyeglasses. The entirety of the functional units 110 to 150 do not have to be combined into a single physical unit. It is possible for the processor 130 and the memory 140 to be contained spatially in another housing and for the different units to communicate with one another either by wire or wirelessly.

The processor 130 is responsible for the image processing, for the detection of objects in the acquired image data and for the projection of the visual information into the field of vision of the operator. Naturally the system 100 can also contain further components, such as units for more precise determination of the position of the system such as acceleration sensors, magnetic field sensors, ultrasound sensors, a light source, e.g. in combination with a photodetector, or RF sources, e.g. in combination with an RF coil. It would be possible for the processor 130 to be embodied to receive corresponding sensor data from one or more sensors in accordance with the aforementioned sensor types. The processor 130 can then be embodied, e.g. to determine the position and/or the orientation of the system in the image data in each case partly on the basis of the sensor data. The scatter field of the magnet 11 of the MR apparatus 10, pre-measured in a calibration routine, could then be measured by the magnetic field sensor, for example. This typically has a characteristic location dependency and can be used for precise positioning. From a comparison of the measured data with reference data obtained from the calibration routine a deduction can then be made about the current position. As an alternative or in addition it would be possible by means of the magnetic field sensor to define changes in direction/rotation of the camera; this can be implemented for example by a change in the measured orientation of the magnetic field for 3D magnetic field sensors or by a change in the strength of the magnetic field, e.g. for 2D magnetic field sensors, e.g. in connection with an acceleration sensor. Further optical aids such as barcodes, labels and similar, which can be acquired by the image acquisition detector 150 and which simplify the precise positioning of the image acquisition detector 150 or of the operator in the room, can be arranged In the room in which the MR apparatus and the system 100 are arranged.

Details of how such a system for displaying an augmented reality, so-called Augmented Reality systems, fundamentally operates for projection of information into a field of vision of a user is known to those skilled in the art and need not be explained in greater detail herein.

As well as the functional units shown, the system 100 can also have a microphone, actuation elements or the like.

The orientation and positioning in the room of the system 100 and thus the field of vision of the operator can be determined while taking account of elements of the medical imaging facility, such as for example of the table 13 and of the MR apparatus or of the housing, the form of which is known to the system 100. When the position and orientation of the MR apparatus in the image data has been recognized by post-processing, location and field of vision of the operator can be deduced. To this end additional position sensors such as ultrasound, light or radio frequency and/or acceleration sensors and/or magnetic field sensors can be used. In particular the movement, i.e. the change in position of the field of vision, can be determined by acceleration sensors or position sensors with the aid of ultrasound, light or radio frequency. The exact positioning and orientation of the operator and thus the knowledge of the sight position is important in order to project the visual information into the field of vision so that it is positioned in a position that corresponds to the way in which the operator sees. If a specific device is to be positioned at a specific location in a next processing step for example, then this device can be projected into the image data as visual information. So that the operator sees the device at the right place however, the sight position, the field of vision of the operator and also the position of objects in the field of vision must be known.

Figure 2:
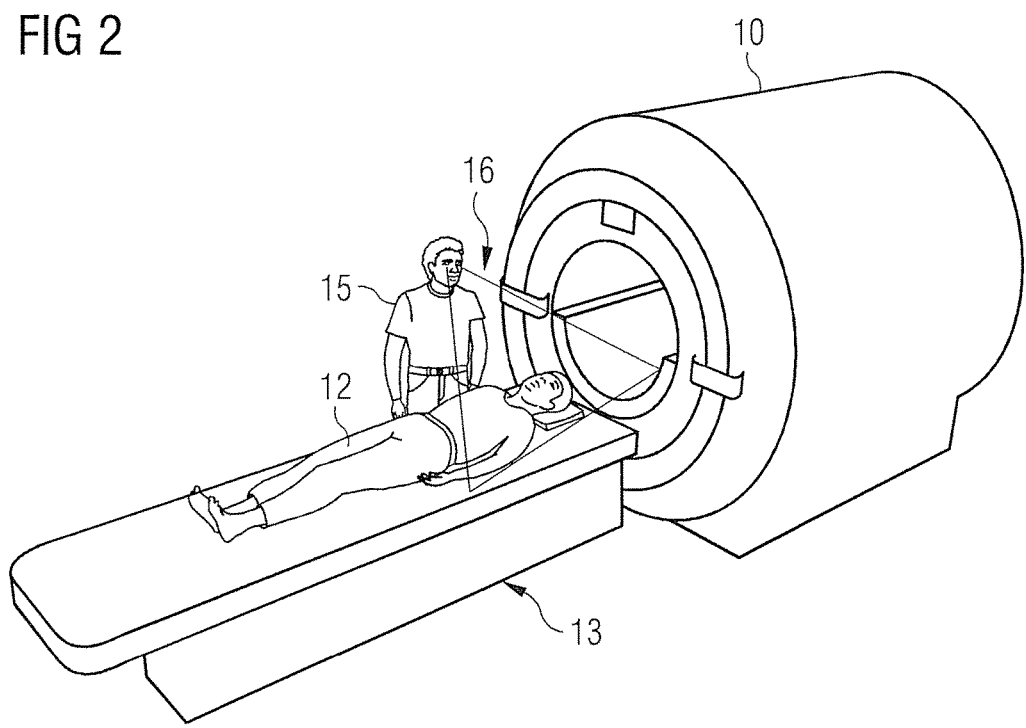
FIG. 2 schematically shows the field of view of an operator, who is looking at an MR apparatus and a person under examination.
Figure 3:
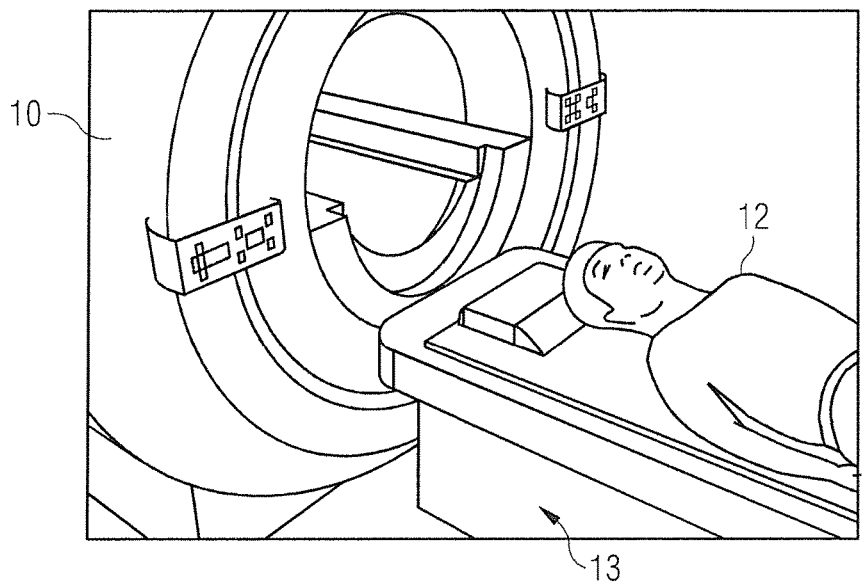
FIG. 3 shows the field of view of the operator in the example from FIG. 2.

FIG. 2 shows schematically how an operator 15 prepares a measurement of a person under examination 12, wherein said person is already arranged on the table 13. Furthermore the field of vision 16 of the operator 15 is shown, wherein this field of vision includes a part of the MR apparatus 10, the person under examination 12, and the patient table 13. In FIG. 3 the situation is now presented as the operator sees it, as namely the operator sees the MR apparatus 10 and the person under examination 12 arranged on the table 13. This field of vision is likewise detected by the image acquisition detector 150. Although the field of vision of the image acquisition detector 150 is slightly shifted, since the image acquisition detector 150 is arranged offset relative to the eyes of the operator, for example on the head or next to the head of the operator, it is still possible to deduce the sight position and the field of vision of the operator from the known position of the image acquisition detector 150 relative to the operator.

Figure 4:
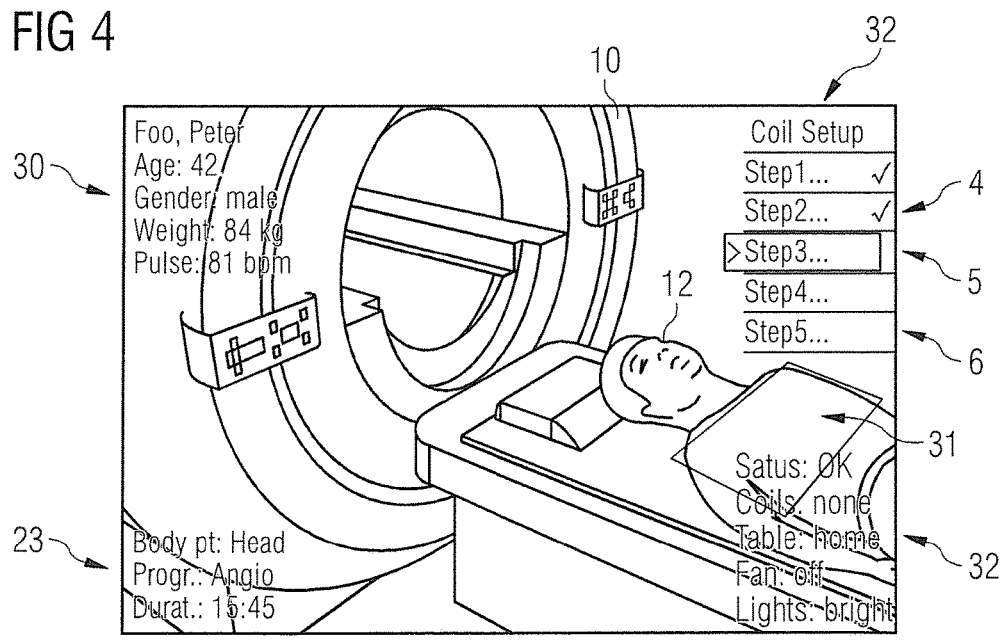
FIG. 4 shows the field of vision of the operator into which the visual information has been projected for better recognition of the next operating step.

FIG. 4 shows how, with the use of the system 100, the operator can be assisted in preparing an MR measurement.

It is now shown in FIG. 4 how the system 100 can support the operator by incorporating various items of information into the field of vision of the operator. In the example shown, an angiography examination of the heart of the person under examination 12 is to be carried out. In the example shown the name of the person under examination is known, for example this has been entered by an operator into the MR apparatus or the name has been extracted from a patient information system. Furthermore it is known which execution sequence protocol is to be carried out. This can result from the medical questionnaire, in the present case MR images of the heart are to be recorded, especially angiography images, i.e. MR images that show the blood flow. For the various medical questionnaires different execution sequence protocols are stored in the memory 27. By calling up and selecting an execution sequence protocol, it is defined which MR examinations are to be carried out, wherein the MR coils needed and the position of the person under examination in the MR apparatus is also defined with said protocol. The MR apparatus can now provide status information to the system 100, for example the information about the table position, the presence of coils or about the execution sequence protocol. In FIG. 4 personal information 30 is shown in the upper left edge of the screen that contains the patient name and patient information, wherein the execution sequence protocol with the various sequence steps is shown as status information 32 in the upper right edge of the screen. In relation to the execution sequence protocol and the associated status information 32 it is further shown which execution sequence steps have already been carried out, in the example shown the steps 1 and 2 are shown as already completed. This information can either come from the MR apparatus or this information is defined by the system 100, for example by image post-processing of the acquired image data, from which for example it can be recognized that the person under examination 12 is already arranged on the table. The status information 32 shown in the right top corner now informs the operator that the next sequence step 3 of the execution sequence protocol is to be carried out. This step 3 contains the placing of the right RF coil at the correct position in the MR apparatus and at the correct position on the person under examination 12. The system 100 now knows the next sequence step to be carried out and knows the field of vision of the operator through the recorded image data that is recorded by the image acquisition detector 150. Thus the system 100 knows the position in the image data at which the operator sees the person under examination. Also the system 100 obtains from the MR apparatus the information that the next step is the positioning of the RF coil, which must be carried out by the operator. The system 100, especially the processor 130, now computes the point in the image data at which the coil is to be projected into the field of vision of the operator as visual information for the operator, so that the operator recognizes immediately how the correct attachment of the coil on the person under examination 12 and on the MR apparatus 10 must be done. Thus visual information 31 is projected into the field of vision at a specific location, namely at the location at which the coil must be attached to the person under examination, as seen by the operator. Furthermore the connection of the coil with the MR apparatus, here with the table 13, is shown.

As further information the system 100 determines the current status of the MR apparatus, wherein said information can be supplied by the MR apparatus or can be determined by the system 100 by image post-processing and detection of objects in the acquired image data. This status information 32 is shown in FIG. 4 at the lower left and right edge of the image and for example contains the name of the execution sequence protocol and the current status of a number of components of the MR apparatus, such as whether RF coils are connected, the position of the table 13 etc.

In the case shown the status information 32 and the personal information 30 are placed so that they disrupt the field of view of the operator as little as possible and are more or less independent of the position of objects in the field of view. The status information and the personal information are preferably displayed in an edge area of the acquired image data, i.e. in a predetermined fixed subarea, while for the positioning of the visual information 31 the precise location and position of the person under examination 12 and of the MR apparatus 10 must be known, so that the coil and the connection element of the coil to the MR apparatus 10 can be projected correctly into the image data. This means that the location of the created visual information relative to the objects recognized in the image data is of importance. The processor 130 computes the location of the visual information relative to objects recognized in the image data, such as the person 12 and the table 13, while the still projected status information and system information is essentially independent of the position of the recognized objects in the image data.

FIG. 5 summarizes the steps that are carried out by the system 100 to create the visual information for the operator. The method starts in step S50 and in a step S51 the execution sequence protocol that is to be carried out in the imaging facility is determined. The execution sequence protocol has a number of steps, such as the positioning of the person under examination, the attachment of objects to the person under examination, such as RF coils for example, or the attachment of other devices, such as ECG electrodes for example, for measuring the heart frequency or a facility for determining the respiratory movement etc. In step S52 the image data are also acquired by the image acquisition detector 150 and from this the field of vision of the operator is determined, so that the system 100 knows how the operator perceives the environment. Likewise the position of objects in the image data are thus determined in the field of vision. Here the sight position and the field of vision of the operator are determined. Furthermore it is determined in a step S53 which operating step must be carried out as the next step by the operator. For this the actual status of the execution sequence protocol is determined, i.e. which sequence steps might possibly already have been carried out. Then the sequence step is determined, especially the sequence step with which an operating step is to be carried out by the operator. If this next operating step is known, it is then possible, in step S54, to determine the associated visual information. In the example of FIG. 4 the next operating step was the attachment of the RF coil. For the determination of the visual information, the position of the MR apparatus, of the person under examination and of the table 13 must be known. Another example is the attachment of ECG electrodes. If the next operating step is the attachment of the electrodes, then the positions of the ECG electrodes on the person under examination 12 can be marked as visual information with electrodes. This can be determined by image post-processing of the acquired image data. When it has now been determined where in the image data and thus where in the field of vision of the operator the person under examination and the patient table are located, it is possible to determine the position of the visual information to be projected and then to project in the visual information at the computed position into the field of vision of the operator (step S55).

The method ends in step S56.

The visual information can also run as a film, for example the visual information is created such that the operator recognizes how the RF coil is laid on the person under examination 12 and how the RF coil is connected to the MR apparatus. This animated presentation facilitates and simplifies the correct execution of the operating step by the operator. Audio information can also be created as well as the visual information for example, which is played to the operator. The audio information can contain instructions, for example as to how the next operating step is to be carried out.

If for example the next operating step to be carried out involves pressing a specific operating element on the imaging facility, then this operating knob can be highlighted visually in the field of vision, by the operating knob flashing for example, or can be highlighted in some other way, so that the operator knows which operating step is to be carried out as the next step.

For many examinations or execution sequence protocols additional devices are needed, for example devices to monitor physiological parameters such as the heartbeat or facilities for injecting contrast media, a respiration belt for determining respiration movement etc. The system 100 can recognize from the acquired image data whether these devices are already arranged in the field of vision at the right position at which they should be present in accordance with the execution sequence protocol. If this is not the case, the operator can still be informed about which of these devices are still missing, wherein device information can be created that is projected into the field of vision, either as general information about which devices are still missing, or specifically about a location at which a device is still missing. The status information presented can also be adapted to the applicable execution sequence protocol, so that only the options are displayed that are possible for the selected execution sequence protocol.

When the execution sequence protocol has been completed, a checklist can be displayed at the end as a further option of the status information, which shows whether all steps to be carried out have been carried out correctly.

Furthermore it is possible that the system recognizes in the acquired image data when operating errors are made. For example if a required subcomponent such as an RF coil has been incorrectly positioned, or if the person under examination was incorrectly positioned on the table. This can be recognized by pattern recognition and image post-processing by the system 100, wherein the system then generates error information that shows the operator where an error has been made in operation, for example the wrongly arranged components can be shown highlighted with the information that an error is present in the highlighted components. The information about the error can also be detected by the imaging facility and transferred to the system 100.

The system 100 can further have an input device, with which the operator can control the MR apparatus, should it be a touch-sensitive interface or other operating elements such as joysticks or control columns, with which parts of the imaging facility, such as the movement of the table for example, can be controlled.

It is shown in conjunction with FIG. 6 how an MR measurement can be carried out using the system 100. The method starts in step S60 and in step S61 the person under examination is registered. In a next step S62 various items of information are collected. This information can come from the memory unit 27 of the MR apparatus, such as for example the selection of the desired execution sequence protocol. Likewise the image data created by the image acquisition detector 150 supplies information that can be evaluated in order to collect information that is necessary to project the visual information at the right location. Furthermore the MR apparatus itself can supply information. As described more precisely in conjunction with FIG. 5, the visual information can then be created and displayed for the operator in step S63, through which a field of vision is produced with a reality augmented by the visual information. This is image data into which the visual information has been projected additionally. In step S64 a check is made as to whether the execution sequence protocol is at an end. If it is not, the system returns to step S62 and the steps S62 to S64 are repeated, until all steps have been carried out. If it is at an end, the MR measurement can be started in step S65.

FIG. 6 shows the interaction of the two systems, i.e. of the MR apparatus 10 and of the system for displaying the augmented reality 100.

As explained above, the present invention makes possible a system for displaying an augmented reality, with which even less highly trained operating personnel can correctly carry out the operating steps to be carried out. Thus the error quota in carrying out the execution sequence protocol can be reduced and the imaging can be accelerated overall. The system for displaying the augmented reality has a processor unit and a memory unit, wherein commands are stored in the memory unit which, when executed by the processor unit, lead to the system carrying out the steps given above.

In another version the system has a processor for determining the execution sequence protocol to be carried out, for acquisition of image data, for determining a next sequence step and the associated operating step. Furthermore, a processor creates the visual information and the projection of the visual information into the field of vision.

With the system described above, the display and control information that are present on the imaging facility itself can be removed or their scope can be reduced, since the necessary information is provided to the operator by the system 100.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatically supporting an operator in proceeding through an execution sequence protocol, comprising multiple sequence steps, with which a patient is being examined in a medical imaging apparatus, said method comprising:
   in a computer, determining the execution sequence protocol to be implemented for said patient;
   with an image data detector, acquiring image data that show a field of vision, as seen by the operator, comprising at least a part of the medical imaging apparatus and the patient;
   in said computer, determining a next sequence step of said execution sequence, which is to be implemented by said operator;
   in said computer, receiving sensor data from a sensor selected from the group consisting of an acceleration sensor, a magnetic field sensor, and ultrasound sensor, a photo detector, and an RF coil;
   in said computer, using said sensor data to determine at least one of a position of the medical imaging apparatus in the image data, an orientation of the medical imaging apparatus in the image data, and a sight position of the operator;
   in said computer, generating visual information that informs said operator about said next sequence step; and
   from said computer, causing said visual information to be projected at a viewing facility, seen by said operator, by displaying augmented reality to the operator in which said field of vision is shown augmented by said visual information, with said visual information being shown at a location in said field of vision that is selected by said computer dependent on said at least one of said position of the medical imaging apparatus in the image data, said orientation of the medical imaging apparatus in the image data, and said sight position of the operator.

2. A method as claimed in claim 1 comprising, in said computer, determining a position of the patient relative to the medical imaging apparatus automatically from said execution sequence protocol, and projecting said position of the patient relative to the medical imaging apparatus in said visual information in said field of vision in said augmented reality.

3. A method as claimed in claim 1 comprising, in said computer, providing personal information about said patient together with said visual information projected into said field of vision in said augmented reality.

4. A method as claimed in claim 1 comprising:
in said computer, automatically determining, from said execution sequence protocol, additional devices that are needed for implementing said execution sequence protocol, and projecting device information about the additionally needed devices into said field of vision in said augmented reality.

5. A method as claimed in claim 4 comprising:
in said computer, determining, from said image data, which of said additionally needed devices is already situated in said field of vision of said operator;
in said computer, determining any of said additionally needed devices that are not present in said field of vision of said operator; and
generating said device information to inform said operator about which of said additionally needed devices are not in said field of vision of said operator.

6. A method as claimed in claim 1 comprising, in said computer, checking said image data to determine whether said image data represent an operating error by detecting a situation for said medical imaging apparatus or said patient that does not match said execution sequence protocol, and projecting error information, describing said operating error, into said field of vision in said augmented reality.

7. A method as claimed in claim 1 comprising converting a description of said next operating step into audio information, and playing said audio information to said operator.

8. A method as claimed in claim 1 comprising employing a magnetic resonance apparatus as said medical imaging apparatus.

9. A method as claimed in claim 8 comprising determining, as said next sequence step to be implemented, positioning of a radio-frequency coil on said patient, and including, in said visual information, a designation of a position to be occupied by said RF coil relative to the magnetic resonance apparatus and the patient.

10. A method as claimed in claim 1 comprising, in said computer, determining a current status of said medical imaging apparatus and generating status information designating said current status, and projecting said status information into said field of vision with said visual information in said augmented reality.

11. A method as claimed in claim 1 comprising, in said computer, determining a location in the image data, relative to at least one other object in said image data, at which the visual information is arranged in the image data, and projecting said visual information at said location into said field of vision in said augmented reality.

12. A system for automatically supporting an operator in proceeding through an execution sequence protocol, comprising multiple sequence steps, with which a patient is being examined in a medical imaging apparatus, said comprising:
a computer configured to determine the execution sequence protocol to be implemented for said patient;
an image data detector that acquires image data that show a field of vision, as seen by the operator comprising at least a part of the medical imaging apparatus and of the patient;
said computer being configured to determine a next sequence step of said execution sequence, which is to be implemented by said operator;
a sensor in communication with said computer, said sensor being selected from the group consisting of an acceleration sensor, a magnetic field sensor, and ultrasound sensor, a photo detector, and an RF coil;
said computer being configured to receive said sensor data and us said sensor data to determine at least one of the position of the medical imaging apparatus in the image data, the orientation of the medical imaging apparatus in the image data, and the sight position of the operator;
said computer being configured to generate visual information that informs said operator about said next sequence step; and
a viewing facility in communication with said computer, said computer being configured to cause said visual information to be projected at said viewing facility, seen by said operator, by displaying augmented reality to the operator in which said field of vision is shown augmented by said visual information, with said visual information being shown at a location in said field of vision that is selected by said computer dependent on said at least one of said position of the medical imaging apparatus in the image data, said orientation of the medical imaging apparatus in the image data, and said sight position of the operator.

13. A system as claimed in claim 12 comprising wherein said computer is configured to determine a position of the patient relative to the medical imaging apparatus automatically from said execution sequence protocol, and projecting said position of the patient relative to the medical imaging apparatus in said visual information in said field of vision in said augmented reality.

14. A system as claimed in claim 12 wherein said computer being configured to provide personal information about said patient together with said visual information projected into said field of vision in said augmented reality.

15. A system as claimed in claim 12 comprising:
said computer is configured to automatically determine, from said execution sequence protocol, additional devices that are needed for implementing said execution sequence protocol, and to project device information about the additionally needed devices into said field of vision in said augmented reality.

16. A system as claimed in claim 15 wherein:
said computer is configured to determine, from said image data, which of said additionally needed devices is already situated in said field of vision of said operator;
said computer is configured to determine any of said additionally needed devices that are not present in said field of vision of said operator; and
said computer is configured to generate said device information to inform said operator about which of said additionally needed devices are not in said field of vision of said operator.

17. A system as claimed in claim 12 wherein said computer is configured to check said image data to determine whether said image data represent an operating error by detecting a situation for said medical imaging apparatus or said patient that does not match said execution sequence protocol, and to project error information, describing said operating error, into said field of vision in said augmented reality.

18. A system as claimed in claim 12 wherein said computer is configured to convert a description of said next operating step into audio information, and to play said audio information to said operator via a speaker in communication with said computer.

19. A system as claimed in claim 12 wherein said medical imaging apparatus is a magnetic resonance apparatus.

20. A system as claimed in claim 19 wherein said computer is configured to determine, as said next sequence step to be implemented, positioning of a radio-frequency coil on said patient, and to include, in said visual information, a designation of a position to be occupied by said RF coil relative to the magnetic resonance apparatus and the patient.

21. A system as claimed in claim 12 wherein said computer is configured to determine a current status of said medical imaging apparatus and to generate status information designating said current status, and to project said status information into said field of vision with said visual information in said augmented reality.

22. A system as claimed in claim 12 wherein said computer is configured to determine a location in the image data, relative to at least one other object in said image data, at which the visual information is arranged in the image data, and to project said visual information at said location into said field of vision in said augmented reality.

\* \* \* \* \*